(12) United States Patent
Caldwell

(10) Patent No.: US 8,701,686 B2
(45) Date of Patent: Apr. 22, 2014

(54) FLOSSING DEVICES AND METHODS OF USING SAME

(76) Inventor: John Larry Caldwell, Sugar Land, TX (US)

(*) Notice: Subject to any disclaimer, the term of this patent is extended or adjusted under 35 U.S.C. 154(b) by 0 days.

(21) Appl. No.: 13/343,413

(22) Filed: Jan. 4, 2012

(65) Prior Publication Data

US 2012/0167913 A1   Jul. 5, 2012

Related U.S. Application Data

(60) Provisional application No. 61/429,802, filed on Jan. 5, 2011.

(51) Int. Cl.
*A61C 15/00*   (2006.01)
(52) U.S. Cl.
USPC .......................................... 132/323
(58) Field of Classification Search
USPC ........ 132/323–327, 329, 321; D28/65, 66, 68
See application file for complete search history.

(56) References Cited

U.S. PATENT DOCUMENTS

| | | | | |
|---|---|---|---|---|
| 2,451,181 A * | 10/1948 | Swartzman | ................... | 132/325 |
| 3,368,553 A * | 2/1968 | Kirby | ........................... | 601/140 |
| 3,789,859 A * | 2/1974 | Chambers | ..................... | 132/326 |
| 4,162,687 A * | 7/1979 | Lorch | ............................ | 132/323 |
| 4,657,033 A | 4/1987 | Dalton | | |
| 5,101,843 A * | 4/1992 | Peng | ............................. | 132/323 |
| 5,692,531 A * | 12/1997 | Chodorow | .................... | 132/323 |
| 6,006,762 A * | 12/1999 | Hsia | .............................. | 132/327 |
| 6,766,808 B2 * | 7/2004 | Gwen | .......................... | 132/323 |
| 7,370,658 B2 * | 5/2008 | Chodorow et al. | .......... | 132/323 |
| 2004/0134512 A1 * | 7/2004 | Ding et al. | .................... | 132/323 |
| 2005/0217692 A1 | 10/2005 | Chodorow et al. | | |
| 2008/0223398 A1 | 9/2008 | Morgan | | |

OTHER PUBLICATIONS

PCT/US2012/020183 International Search Report and Written Opinion dated Aug. 7, 2012 (10 p.).

* cited by examiner

*Primary Examiner* — Todd Manahan
*Assistant Examiner* — Brianne Kalach
(74) *Attorney, Agent, or Firm* — Conley Rose, P.C.

(57) ABSTRACT

A device for flossing teeth comprises an elongate handle having a central axis. In addition, the device comprises a head including a pair of spaced apart posts and a base portion extending therebetween. Each post has a central axis. The central axis of each post is disposed in a plane that is oriented at an acute angle β in side view relative to a projection of the central axis of the handle. Further, the device comprises a neck extending between the handle and the base portion of the head. The device also comprises a strand of floss extending between the posts.

21 Claims, 5 Drawing Sheets

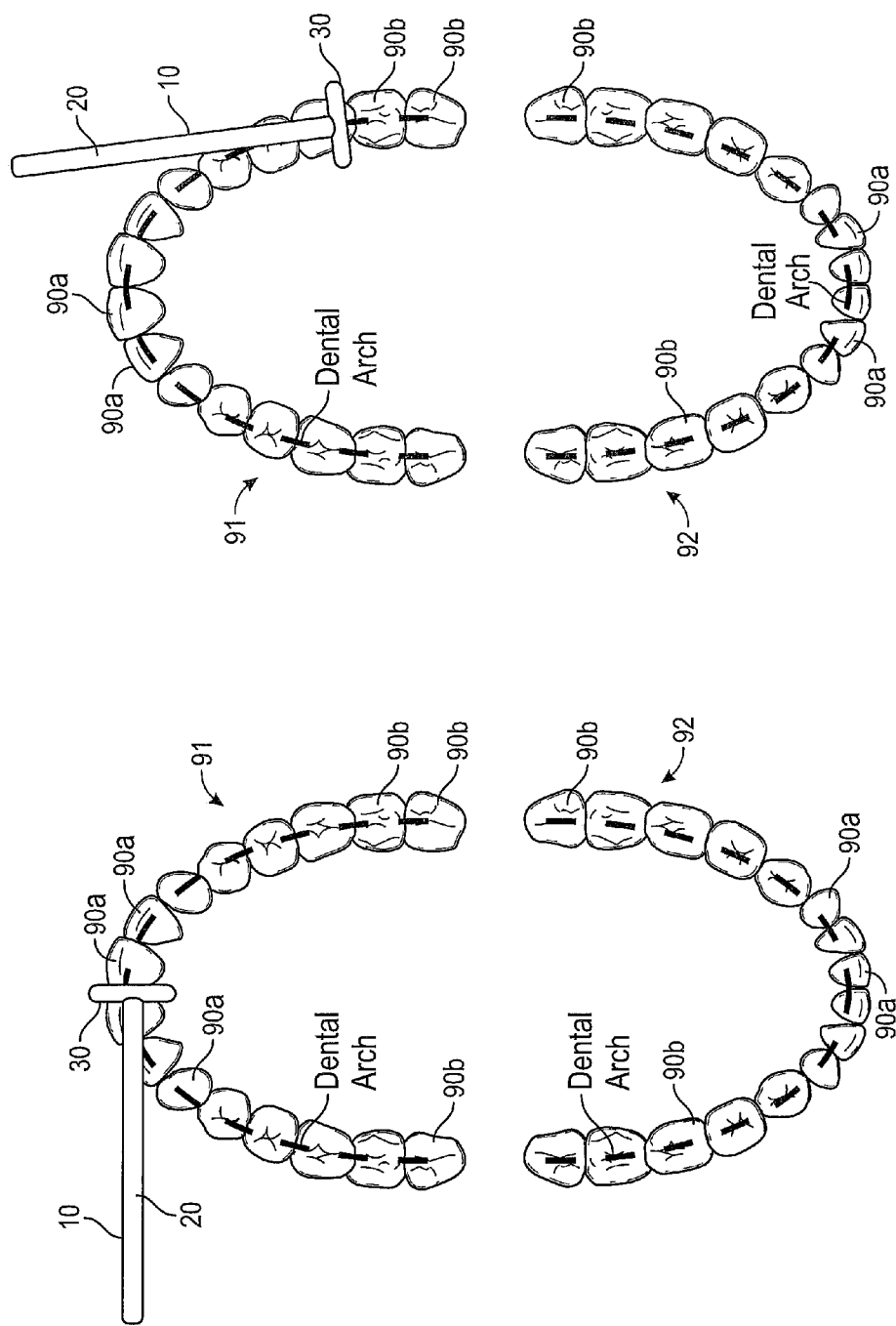

FLOSSING DEVICES AND METHODS OF USING SAME

CROSS-REFERENCE TO RELATED APPLICATIONS

This application claims benefit of U.S. provisional patent application Ser. No. 61/429,802 filed Jan. 5, 2011, and entitled "Flossing System with a Periodontic or Orthodontic Attachment," which is hereby incorporated herein by reference in its entirety.

STATEMENT REGARDING FEDERALLY SPONSORED RESEARCH OR DEVELOPMENT

Not applicable.

BACKGROUND

1. Field of the Invention

The invention relates generally to devices for flossing teeth. More particularly, the invention relates to a handheld flossing devices for ease of use in conjunction with orthodontic braces.

2. Background of the Technology

Flossing removes food and dental plaque from teeth, and is essential to good oral hygiene. While brushing is an effective way to clean teeth, it reaches only about sixty percent of the surfaces of teeth. Flossing is needed to reach areas of the teeth that brushing cannot, in particular the areas between teeth.

Typically, floss is placed in tension between the users hands, and gently inserted between the teeth. Once positioned between the teeth, the floss is moved up and down to scrape along the teeth sides, particularly close to the gums. However, accessing those areas close to the gums using conventional floss can be difficult, especially when orthodontic braces are present.

More advanced flossing devices such as the Platypus™ Orthodontic Flosser available from Platypus Co. of Missoula, Mont. include a handle and a head attached to one end of the handle. The head includes two generally straight posts and a segment of floss extending between the posts. The handle, posts, and floss are generally lie in a common plane. Thus, one of the two posts is position proximal the handle (the proximal post) and the other post is positioned distal the handle (the distal post). To align the floss segment with the gap between a pair of adjacent teeth, the floss segment and handle are generally oriented parallel to the gap (i.e., parallel to the lateral sides of the adjacent teeth) and perpendicular to the dental arch and gums in the region to be flossed. Then, the handle is manipulated to advance the floss segment up and down between the adjacent teeth. For anterior teeth positioned near the front of the mouth (e.g., incisors and canines), positioning and moving the floss segment in this manner can be performed with relative ease. However, for posterior teeth positioned near the rear of the mouth (e.g., premolars and molars), positioning and moving the floss segment in this manner is more challenging due to interference between the handle and the user's cheek.

The Platypus™ Orthodontic Flosser can be used in conjunction with orthodontic braces. In particular, the distal post is positioned inside the mouth (i.e., inside the dental arch) while the proximal post is positioned adjacent the gums between the teeth and archwire (i.e., outside the dental arch). Then, the handle is manipulated to advance the floss segment up and down between the adjacent teeth. However, since the proximal post is generally straight and in close proximity to the gums in order to be positioned between the archwire and the teeth, the tip of the proximal post may strike the gums, potentially resulting in pain, discomfort, gum irritation, and bleeding.

Accordingly, there remains a need in the art for flossing devices suited for flossing both anterior and posterior teeth with ease. Such flossing devices would be particularly well-received if they could be employed in conjunction with braces with reduced likelihood of gum impingement.

BRIEF SUMMARY OF THE DISCLOSURE

These and other needs in the art are addressed in one embodiment by a device for flossing teeth. In an embodiment, the device comprises an elongate handle having a central axis. In addition, the device comprises a head including a pair of spaced apart posts and a base portion extending therebetween. Each post has a central axis. The central axis of each post is disposed in a plane that is oriented at an acute angle β in side view relative to a projection of the central axis of the handle. Further, the device comprises a neck extending between the handle and the base portion of the head. Still further, the device comprises a strand of floss extending between the posts.

These and other needs in the art are addressed in another embodiment by a device for flossing teeth. In an embodiment, the device comprises an elongate handle having a central axis. In addition, the device comprises a head including a first post, a second post substantially parallel to the first post and spaced apart from the first post, and a base portion extending from the first post to the second post. Each post has a first end attached to the base portion and a second end distal the base portion. The second end of the first post comprises a prong that is angled away from the second post. The second end of the second post comprises a prong that is angled away from the first post. Further, the device comprises a neck extending between the handle and the base portion of the head. Still further, the device comprises a strand of floss extending between the posts.

Embodiments described herein comprise a combination of features and advantages intended to address various shortcomings associated with certain prior devices, systems, and methods. The various characteristics described above, as well as other features, will be readily apparent to those skilled in the art upon reading the following detailed description, and by referring to the accompanying drawings.

BRIEF DESCRIPTION OF THE DRAWINGS

For a detailed description of the preferred embodiments of the invention, reference will now be made to the accompanying drawings in which:

FIG. 5A is a schematic view illustrating the flossing apparatus of FIG. 1 being used to floss anterior teeth at the front of the mouth; and FIG. 5B is a schematic view illustrating the flossing apparatus of FIG. 1 being used to floss posterior teeth at the rear of the mouth.

DETAILED DESCRIPTION

Figure 1:
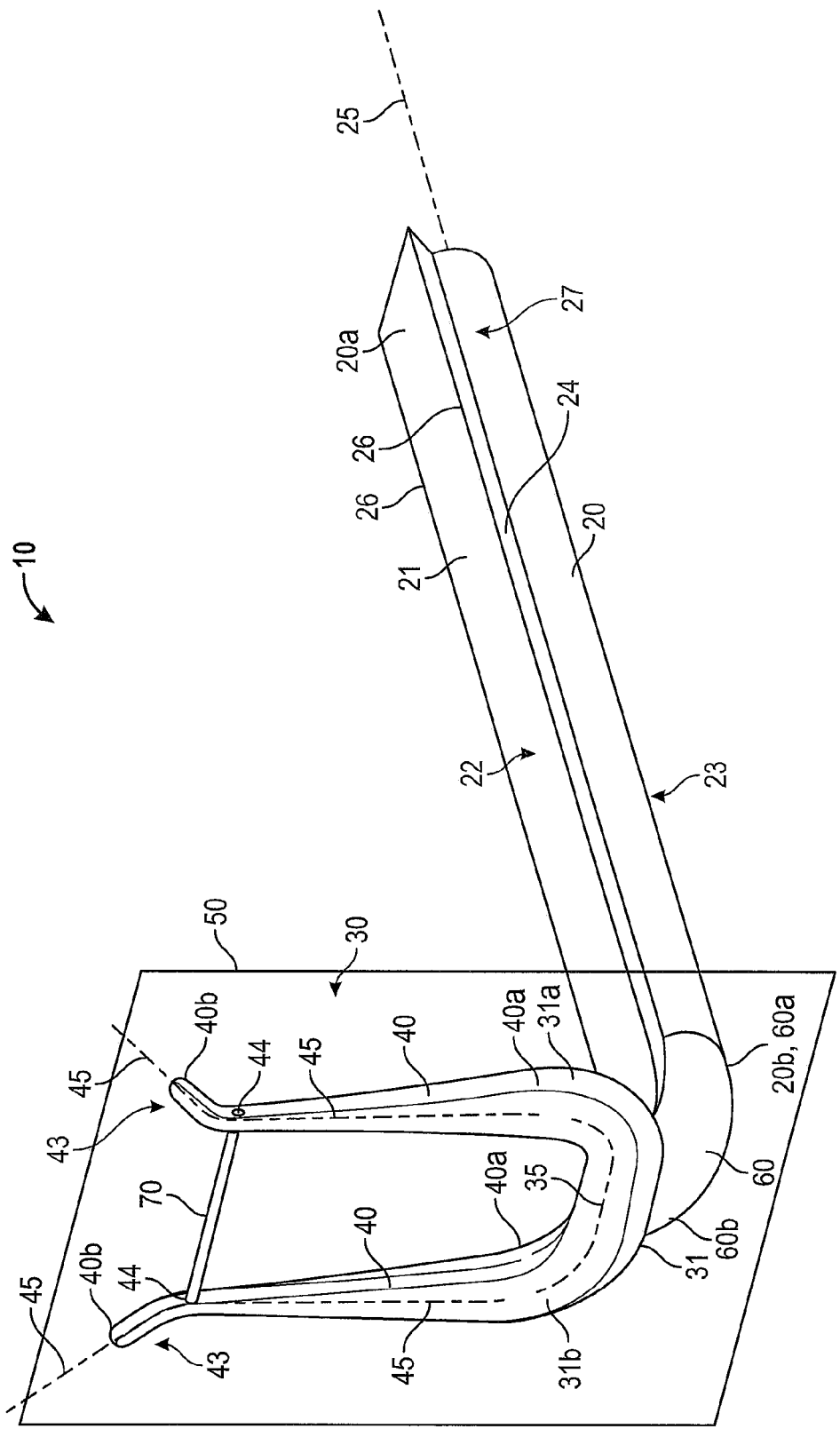
FIG. 1 is a side perspective rear view of an embodiment of a flossing apparatus in accordance with the principles disclosed herein.

The following discussion is directed to various exemplary embodiments. However, one skilled in the art will understand that the examples disclosed herein have broad application, and that the discussion of any embodiment is meant only to be exemplary of that embodiment, and not intended to suggest that the scope of the disclosure, including the claims, is limited to that embodiment.

Certain terms are used throughout the following description and claims to refer to particular features or components. As one skilled in the art will appreciate, different persons may refer to the same feature or component by different names. This document does not intend to distinguish between components or features that differ in name but not function. The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection, or through an indirect connection via other devices, components, and connections. In addition, as used herein, the terms "axial" and "axially" generally mean along or parallel to a central axis (e.g., central axis of a body or a port), while the terms "radial" and "radially" generally mean perpendicular to the central axis. For instance, an axial distance refers to a distance measured along or parallel to the central axis, and a radial distance means a distance measured perpendicular to the central axis.

Figure 2:
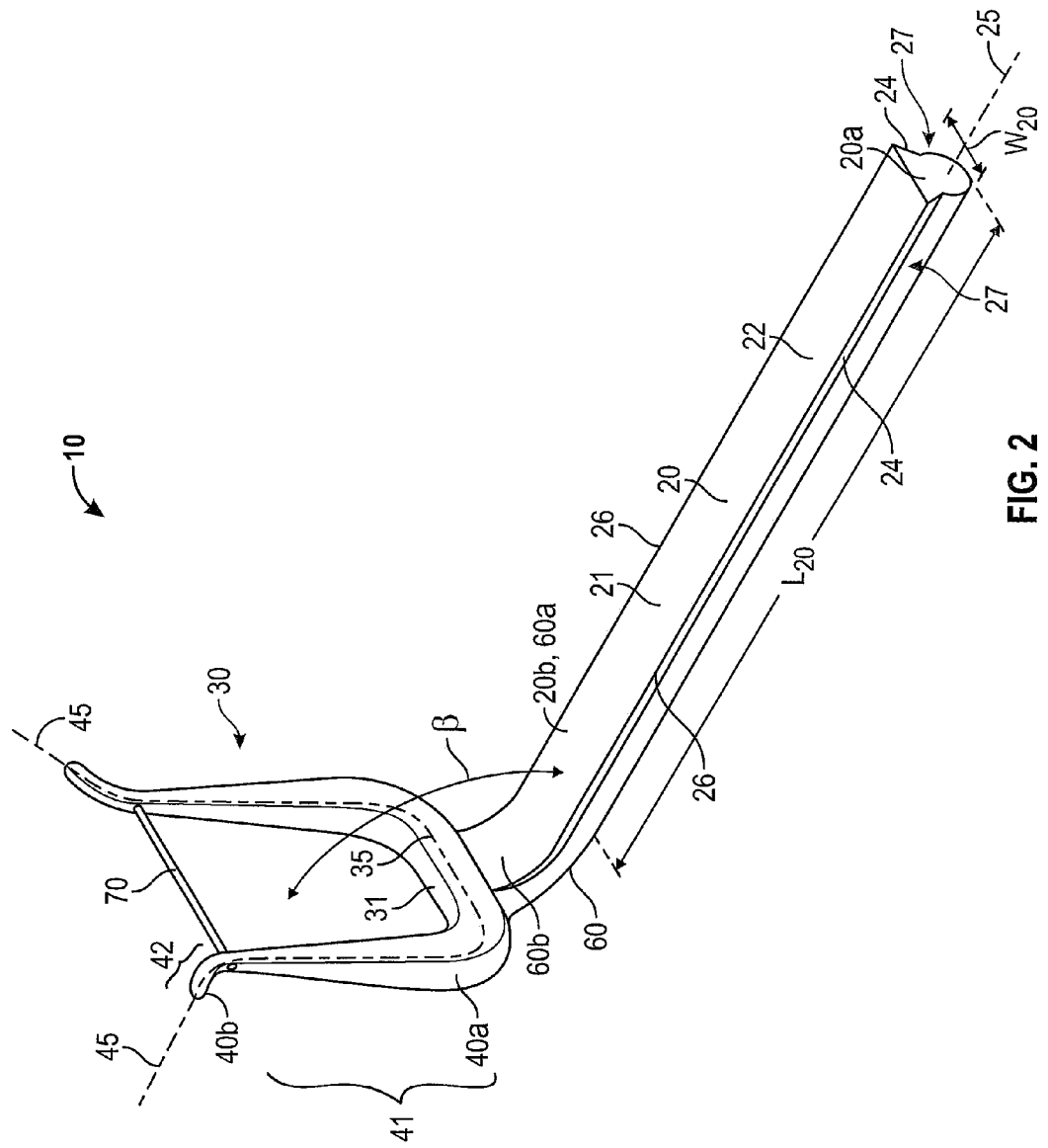
FIG. 2 is a rear perspective view of the flossing apparatus of FIG. 1.
Figure 3:
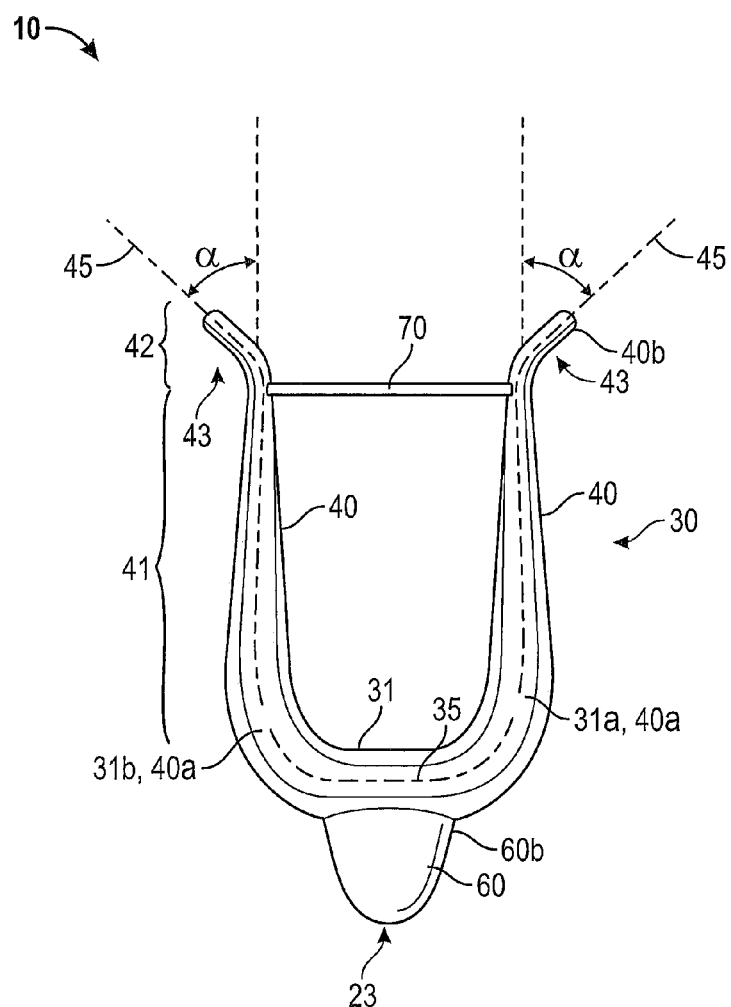
FIG. 3 is a front view of the flossing apparatus of FIG. 1.
Figure 4:
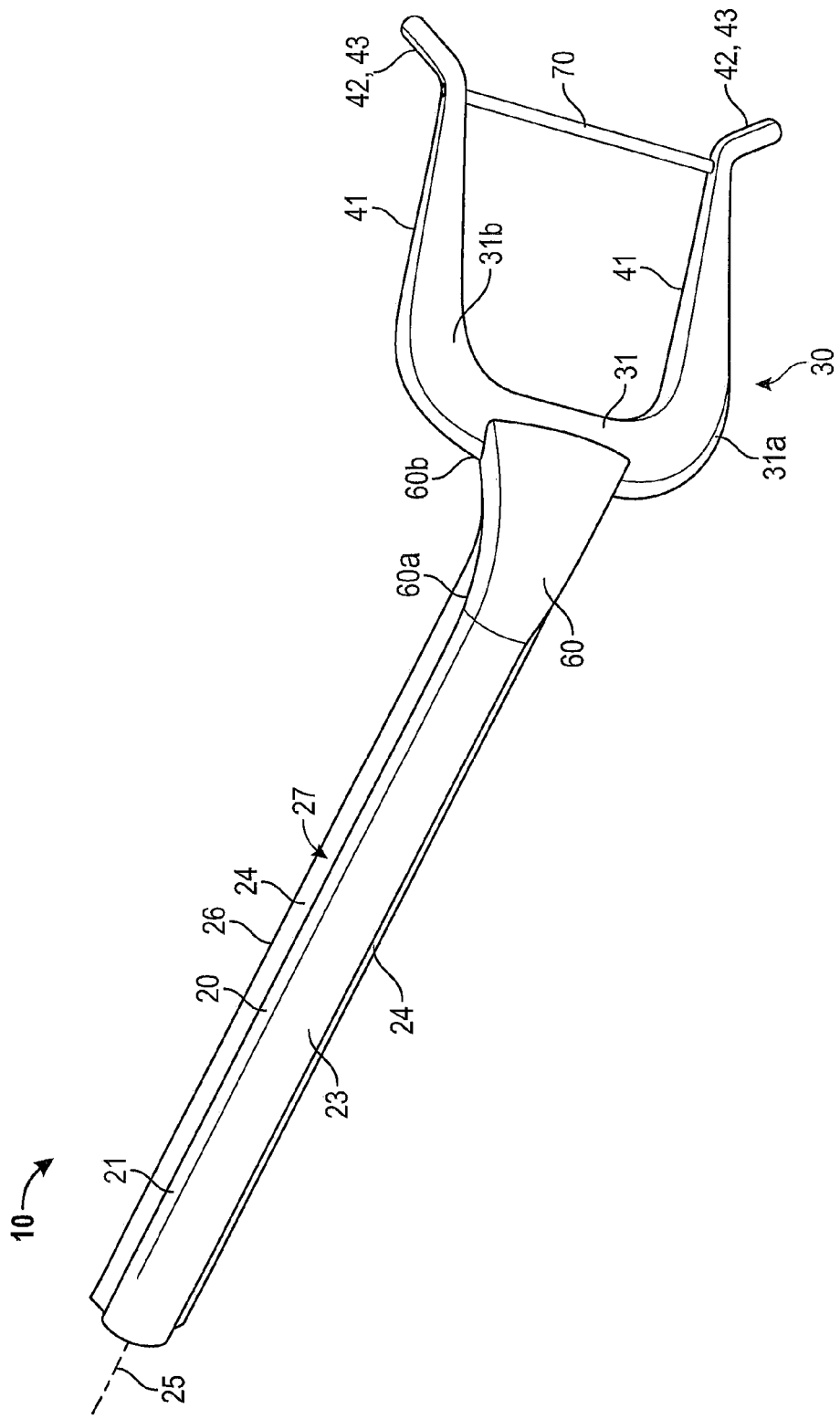
FIG. 4 is a bottom perspective view of the flossing apparatus of FIG. 1.

Referring now to FIGS. 1-4, a flossing device 10 in accordance with the principles disclosed herein is shown. In this embodiment, flossing device 10 includes a handle 20, a head 30, and an arcuate neck 60 extending between handle 20 and head 30. As shown, handle 20, head 30, and neck 60 comprise a single-piece structure that is monolithically formed (i.e., cast or mold as a single piece). However, in other embodiments, the handle (e.g., handle 20), the head (e.g., head 30), the neck (e.g., neck 40), or combinations thereof may be formed separately and subsequently attached to each other. In general, handle 20, head 30, and neck 60 may comprise any material suitable for use in the mouth such as metal or metal alloys, polymers, or composites. To simplify manufacturing and reduce related costs, handle 20, head 30, and neck 60 preferably comprise a plastic material.

Handle 20 has a straight central or longitudinal axis 25, a first or free end 20a, and a second or fixed end 20b opposite end 20a. In addition, handle 20 has a radially outer surface 21 extending between ends 20a, b. In this embodiment, outer surface 21 includes a planar upper surface 22, a rounded semi-circular lower surface 23, and a pair of planar flanks 24 extending from upper surface 22 to lower surface 23. Flanks 24 taper inward moving from upper surface 22 to lower surface 23, thereby defining lateral edges 26 on handle 20 between flanks 24 and upper surface 22 and concave lateral recesses 27 on handle 20 between flanks 24 and lower surface 23. Edges 26 and recesses 27 extend axially between ends 20a, b of handle. The different contours of surfaces 22, 23, lateral edges 26, and lateral recesses 27 provide texture to handle 20 to facilitate gripping and manipulation of handle 20 and device 10 during flossing. Handle 20 has a length $L_{20}$ measured axially between ends 20a, b and a width $W_{20}$ measured perpendicular to axis 25 in top view between lateral edges 26. Length $L_{20}$ is substantially greater than width $W_{20}$, and thus, handle 20 may be described as an "elongate" body or structure.

Head 30 of device 10 is a generally U-shaped structure including a base portion 31 and a pair of spaced-apart generally parallel extensions or posts 40 extending from base portion 31. In this embodiment, each post 40 extends generally perpendicularly from base portion 31. Base portion 31 has a central or longitudinal axis 35, a first end 31a contiguous with one post 40, and a second end 31b contiguous with the other post 40.

Each post 40 has a central or longitudinal axis 45, a first or fixed end 40a, and a second or free end 40b opposite end 40a. Posts 40 are spaced apart a minimum distance $D_{40}$ measured between posts 40. In embodiments described herein, distance $D_{40}$ is preferably between 12 mm and 14 mm. In this embodiment, each post 40 tapers (i.e., its cross-sectional area decrease) moving along its corresponding axis 45 from end 40a to end 40b. First end 40a of each post 40 is connected to one end 31a, b of base portion, whereas second end 40b of each post 40 is not connected to any other structures or components. In this embodiment, axes 35, 45 of base portion 31 and posts 36, respectively, each lie in a common plane 50.

Each post 40 has a first portion 41 extending from end 40a and a second portion 42 extending from first portion 41 to end 40b. Second portion 42 of each post 40 is oriented at an angle α relative to first portion 41, thereby defining an outwardly flared prong or tip 43 at each end 40b. Although axis 45 is straight along first portion 41 and straight along second portion 42, axis 45 is bent at the transition from first portion 41 to second portion 42. In particular, within second portion 42, axis 45 is oriented at an angle α relative to a projection of axis 45 in first portion 41. In this embodiment, tip 43 of each post 40 is angled outward relative to the other post 40. In embodiments described herein, angle α is preferably an acute angle between 30° and 60°, and more preferably 45°. In this embodiment, angle α is 45°.

A piece or strand of floss 70 extends between posts 40 distal base portion 31. The ends of floss 70 are fixably secured to posts 40 such that tension may be applied to floss 70 without the ends of floss 70 detaching from posts 40. In this embodiment, each post 40 includes a through bore 44 in first portion 41 axially adjacent flared tip 43. Bores 44 in posts 40 are aligned, floss 70 extends through both bores 44, and the ends of floss 70 are fused (e.g., melted) to the outer surface of posts 40. Thus, in this embodiment, floss 70 extends through both posts 40.

Referring still to FIGS. 1-4, neck 60 connects handle 20 and head 30. In particular, neck 60 has a first end 60a connected to end 20b of handle 20 and a second end 60b connected to base portion 31 of head 30. In this embodiment, second end 60b is positioned at the midpoint of base portion 31 between ends 31a, b. In addition, neck 60 is tapered, having a width and cross-sectional area that increases moving along the length of neck 60 from end 60a to end 60b. Such a tapered neck 60 offers the potential to enhance the strength and structural integrity of device 10 in the region proximate the connection between handle 20 and head 30, thereby reducing the potential for inadvertent separation or breakage of head 30 from handle 20 during use of device 10.

Neck 60 bends or curves along its length as it extends from handle 20 to head 30, thereby enabling head 30 and plane 50 to be oriented at an angle β relative to a projection of axis 25 of handle 20. Angle β is preferably between 75° and 105° and more preferably 90°. In this embodiment, plane 50 is orthogonal to a projection of axis 25.

Referring now to FIGS. 5A and 5B, flossing device 10 is schematically shown flossing between teeth 90a at the anterior of the upper arch 91 (FIG. 5A) and teeth 90b at the posterior of the upper arch 91 (FIG. 5B). To floss teeth 90a, b of upper arch 91, the user grasps handle 20 and positions handle 20 generally horizontal and head 30 generally vertical with floss strand 70 disposed above base portion 41. While maintaining handle 20 generally horizontal and head 30 generally vertical, the user positions tips 43 on opposite sides of the dental arch with floss strand 70 aligned with and immediately below the gap between the pair of adjacent teeth 90a, b to be flossed. As shown in FIGS. 5A and 5B, whether flossing anterior teeth 90a or posterior teeth 90b, to position floss strand 70 in this manner, handle 20 is oriented generally tangent to the dental arch in the region to be flossed. Next, using handle 20, the users urges device 10 upward to advance floss strand 70 between the teeth 90a, b to be flossed, and then, moves floss strand 70 up and down between teeth 90a, b. In addition, or alternatively, the user may rock head 30 and floss strand 70 back and forth between teeth 90a, b by generally rotating device 10 about axis 25 of handle 20. Although device 10 has been shown and described as flossing teeth 90a, b of upper arch 91. Device 10 is used in the same manner to floss teeth at the anterior and posterior of lower arch 92, with the exception that device 10 is flipped upside down (i.e., rotated 180° about axis 25) to position floss strand 70 below base portion 41.

As previously described and illustrated in FIGS. 5A and 5B, to floss anterior teeth 90a or posterior teeth 90b, handle 20 is oriented generally tangent to the dental arch in the region to be flossed. Thus, when flossing anterior teeth 90a, handle 20 extends generally laterally from the mouth (i.e., axis 25 is generally oriented perpendicular to the sagittal plane and parallel to the coronal plane) as shown in FIG. 5A, and when flossing posterior teeth 90b, handle 20 extends generally ventrally outward from the mouth (i.e., axis 25 is generally oriented parallel to the sagittal plane and perpendicular to the coronal plane) as shown in FIG. 5B. As a result, there is little to no interference between the user's cheeks and handle 20 while flossing posterior teeth 90b, and although handle 20 extends laterally while flossing anterior teeth 90a, there is sufficient clearance in the anterior of the mouth to accommodate handle 20 without any interference. It should be appreciated that the orientation of handle 20 generally tangent to the dental arch in the region to be flossed is in stark contrast to most conventional flossing devices that require the handle to be positioned perpendicular to the dental arch in the region to be flossed. Accordingly, embodiments described herein offer the potential to enhance ease of flossing by reducing interference between the handle (e.g., handle 20) and the user's cheeks.

Device 10 may also be used in substantially the manner as previously described to floss around braces. In particular, the user grasps handle 20 and positions handle 20 generally horizontal and head 30 generally vertical with (a) floss strand 70 disposed above base portion 41 for flossing teeth 90a, b disposed in the upper arch 91, or (b) floss strand 70 disposed below base portion 41 for flossing teeth 90a, b disposed in the lower arch 92. While maintaining handle 20 generally horizontal and head 30 generally vertical, the user positions tips 43 on opposite sides of the dental arch with floss strand 70 aligned with and immediately below the gap between the pair of adjacent teeth 90a, b to be flossed. With braces present, tip 43 disposed on the outside of the dental arch is positioned between the archwire and teeth 90a, b proximal the gum. Next, using handle 20, the users urges device 10 upward (to floss between teeth 90a, b disposed in the upper arch 91) or downward (to floss teeth 90a, b disposed in the lower arch 92) to advance floss strand 70 between the teeth 90a, b to be flossed. To thread flared tip 43 between the archwire and teeth 90a, b, the user may rotate device 10 about axis 25 of handle 20 (raising the inner post 40 upward relative to the outer post 40) to orient tip 43 substantially vertical and initially positioned end 40b between the archwire and teeth 90a, b, and then rotate device about axis 25 in the opposite direction (lowering the inner post 40 upward relative to the outer post 40) as floss strand 70 is advanced between teeth 90a, b. With floss strand 70 disposed between teeth 90a, b, floss strand 70 is moved up and down between teeth 90a, b using handle 20. In addition, or alternatively, the user may rock head 30 and floss strand 70 back and forth between teeth 90a, b by generally rotating device 10 about axis 25 of handle 20. As previously described, posts 40 of device 10 include tips 43 that are flared outward and disposed at angle α. Consequently, embodiments described herein offer the potential to reduce gum impingement with tips 43 of posts 40 as compared to many conventional flossing devices with generally straight posts.

While preferred embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the invention. For example, the relative dimensions of various parts, the materials from which the various parts are made, and other parameters can be varied. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simply subsequent reference to such steps.

What is claimed is:

1. A device for flossing teeth, comprising:
    an elongate handle having a central axis, a first end, a second end opposite the first end, a planar upper surface extending between the first end to the second end, and a curved convex lower surface extending from the first end to the second end, and a pair of flank surfaces extending from the upper surface to the lower surface;
    a head including a first post, a second post spaced apart from the first post, and a base portion extending between the first post and the second post, wherein each post has a central axis and a throughbore extending through the post, wherein the base portion of the head is coupled to the second end of the handle;
    wherein the central axis of each post is disposed in a plane that is oriented at an angle β between 75° and 105° in side view relative to a projection of the central axis of the handle;
    wherein each post has a first end connected to the base portion and a second end distal the base portion;
    wherein the second end of each post comprises a tip, wherein the tip of the first post and the tip of the second post flare outwardly away from each other;
    wherein each post tapers continuously moving from the first end to the second end;
    a neck extending between the handle and the base portion of the head; and a strand of floss extending between the first post and the second post;

wherein the strand of floss has a first end extending through the throughbore in the first post and a second end extending through the throughbore in the second post;

wherein the first end of the strand of floss is fused to the first post and the second end of the strand of floss is fused to the second post.

2. The device of claim 1, wherein the plane is oriented perpendicular to the projection of the central axis of the handle.

3. The device of claim 2, wherein the first post and the second post are spaced apart a minimum distance of at least 12 mm.

4. The device of claim 3, wherein the minimum distance is between 12 mm and 14 mm.

5. The device of claim 1, wherein each post comprises a first portion extending from the corresponding first end to the corresponding tip;

wherein the tip of each post is oriented at an angle α relative to the first portion of the corresponding post;

wherein the angle α is between 30° and 60°.

6. The device of claim 5, wherein the angle α is 45°.

7. The device of claim 1, wherein the head, the neck, and the handle are monolithically formed.

8. The device of claim 1, wherein the neck tapers moving from the base portion of the head to the handle.

9. A device for flossing teeth, comprising:

an elongate handle having a central axis, a first end, a second end opposite the first end, a planar upper surface extending between the first end to the second end, and a curved convex lower surface extending from the first end to the second end, and a pair of flank surfaces extending from the upper surface to the lower surface;

a head including a first post, a second post substantially parallel to the first post and spaced apart from the first post, and a base portion extending from the first post to the second post, wherein the base portion of the head is coupled to the second end of the handle;

wherein each post has a first end attached to the base portion, a second end distal the base portion, an elbow positioned between the first end and the second end, a first portion extending from the first end to the elbow, and a second portion extending from the elbow to the second end;

wherein the second portions of the posts flare outwardly away from each other;

wherein the second portion of the first post is oriented at an acute angle α1 relative to the first portion of the first post, and the second portion of the second post is oriented at an acute angle α2 relative to the first portion of the second post;

a neck extending between the handle and the base portion of the head; and a strand of floss extending between the posts, wherein the strand of floss has a first end attached to the first portion of the first post and a second end attached to the first portion of the second post.

10. The device of claim 9, wherein each post has a central axis;

wherein the central axis of each post lies in a common plane that is oriented at an angle β between 75° and 105° relative to a projection of the central axis of the handle.

11. The device of claim 10, wherein the base portion has a central axis that lies in the common plane, and wherein the common plane is orthogonal to the projection of the central axis of the handle.

12. The device of claim 9, wherein the posts are spaced apart a minimum distance between 12 mm and 14 mm.

13. The device of claim 9, wherein the angle α1 and the angle α2 are each between 30° and 60°.

14. The device of claim 13, wherein each angle α1 and α2 is 45°.

15. The device of claim 9, wherein each post includes a throughbore positioned axially adjacent the corresponding second portion, wherein the strand of floss has a first end extending through the throughbore in the first post and a second end extending through the throughbore in the second post.

16. The device of claim 9, wherein the head, the neck, and the handle are monolithically formed.

17. The device of claim 9, wherein the neck tapers moving from the base portion of the head to the handle.

18. The device of claim 9, wherein each post tapers moving away from the base portion.

19. The device of claim 5, wherein the throughbore in the first post is axially adjacent an intersection of the first portion and the second portion of the first post; and wherein the throughbore in the second post is axially adjacent an intersection of the first portion and the second portion of the second post.

20. The device of claim 19, wherein the first portion of the first post extends linearly from the first end of the first post to the second portion of the first post;

wherein the first portion of the second post extends linearly from the first end of the second post to the second portion of the second post;

wherein the second portion of the first post extends linearly from the second end of the first post to the first portion of the first post;

wherein the second portion of the second post extends linearly from the second end of the second post to the first portion of the second post.

21. The device of claim 9, wherein the first end of the strand of floss is coupled to the first post adjacent the elbow in the first post, and wherein the second end of the strand of floss is coupled to the second post adjacent the elbow in the second post.

* * * * *